(12) United States Patent
Konopa et al.

(10) Patent No.: US 6,229,015 B1
(45) Date of Patent: May 8, 2001

(54) ACRIDONE DERIVATIVES AND METHOD OF PREPARATION OF 8-HYDROXY IMIDAZOACRIDINONE DERIVATIVES

(75) Inventors: Jerzy Kazimierz Konopa; Marek Tadeusz Konieczny, both of Gdańsk (PL)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/286,655

(22) Filed: Apr. 6, 1999

Related U.S. Application Data

(63) Continuation of application No. PCT/GB97/02470, filed on Sep. 10, 1997.

(30) Foreign Application Priority Data

Oct. 7, 1996 (GB) .................................................. 9620751

(51) Int. Cl.⁷ ...................... C07D 471/04; C07D 219/06; C07D 219/08
(52) U.S. Cl. .............................................. 546/66; 546/103
(58) Field of Search ........................................ 546/66, 103

(56) References Cited

FOREIGN PATENT DOCUMENTS 0 502 668 A1   9/1992 (EP) .
92 15583       9/1992 (WO) .

OTHER PUBLICATIONS

Cholody et al, "Chromophore–Modified Antineoplastic . . . ," J. Med. Chem., vol. 35, pp. 378–382 (1992).
Cholody et al,, "Synthesis of Substituted 1,4–Diazepino . . . ," J. Heterocyclic Chem., vol. 29, p. 1749 (1992).

Primary Examiner—Alan L. Rotman
(74) Attorney, Agent, or Firm—Nixon & Vanderhye

(57) ABSTRACT

A process of preparing a compound of formula (I):

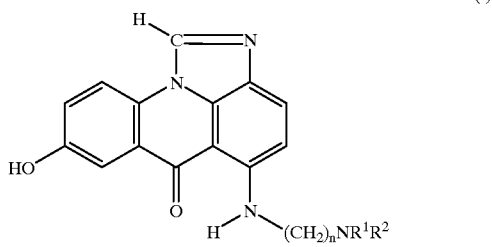

(I)

wherein $R^1$ and $R^2$ are alkyl groups of 1 to 4 carbon atoms and n is from 2 to 5, comprises reacting a 1-chloro-7-(protected hydroxy)-4-nitroacridin-9(10H)-one of formula (IV-P):

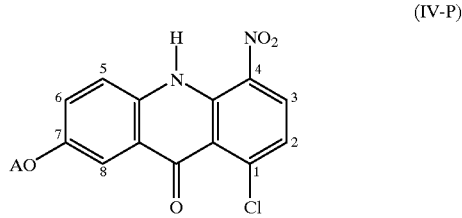

(IV-P)

wherein A is a hydroxy-protecting group removable by reduction, with an ω-(dialkylamino)alkylamine of formula $$NH_2-(CH_2)_n NR^1R^2$$

in which n, $R^1$ and $R^2$ are as defined above, to produce a 7-(protected hydroxy)4-nitro-1-[[ω-(dialkylamino)alkyl]amino]acridin-9(10H)-one (III-P), reducing the compound III-P at a temperature of from 15 to 50° C. with a hydrogen gas or with formate ions, in the presence of a palladium catalyst and formic acid, removing substantially all the residual palladium and heating the remaining reaction mixture to effect cyclization to the corresponding compound of formula (I). If desired, after removal of the palladium the intermediate 7-hydroxy-4-N-formyl-1-[[ω-(dialkylamino)alkyl]amino]acridin]-9(10H)-one can be isolated and subsequently cyclized by heating. Such compounds have antineoplastic activity.

11 Claims, No Drawings

ACRIDONE DERIVATIVES AND METHOD OF PREPARATION OF 8-HYDROXY IMIDAZOACRIDINONE DERIVATIVES

The present application is a continuation of PCT/GB97/02470, filed Sep. 10, 1997.

BACKGROUND OF THE INVENTION

1. Technical Field of the Invention

The invention relates to a process for the preparation of (5-[[ω-(dialkylamino)alkyl]amino]-8-hydroxyimidazo[4,5,1-de]acridin-6-ones of general formula (I),

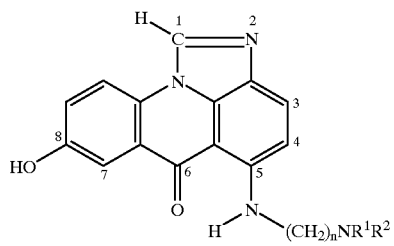

wherein $R^1$ and $R^2$ represent alkyl groups of 1 to 4 carbon atoms which may be the same or different and n is 2 to 5.

These compounds show anti-neoplastic activity, in particular against leukaemia, melanomas or colon adenocarcinomas, as more fully set forth in Z. Mazerska et al., Anti-Cancer Drug Design 11, 73–88 (1996).

The invention further relates to certain new 1-[[ω-(dialkylamino)alkyl]amino]-4-substituted-7-hydroxyacridin-9(10H)-ones, useful as intermediates in the process of the invention and also having anti-neoplastic activity.

2. Description of the Related Art

Methods of preparation of the imidazoacridinones of general formula I are known from PCT Application WO-A-92/15583 and W. Cholody et al. J. Med. Chem 35, 378–382 (1992), and depend on cyclisation of amines of general formula (II). The amines (II) can be prepared by a multi step process, as described in the above patent application and shown in Scheme 1:

Scheme 1

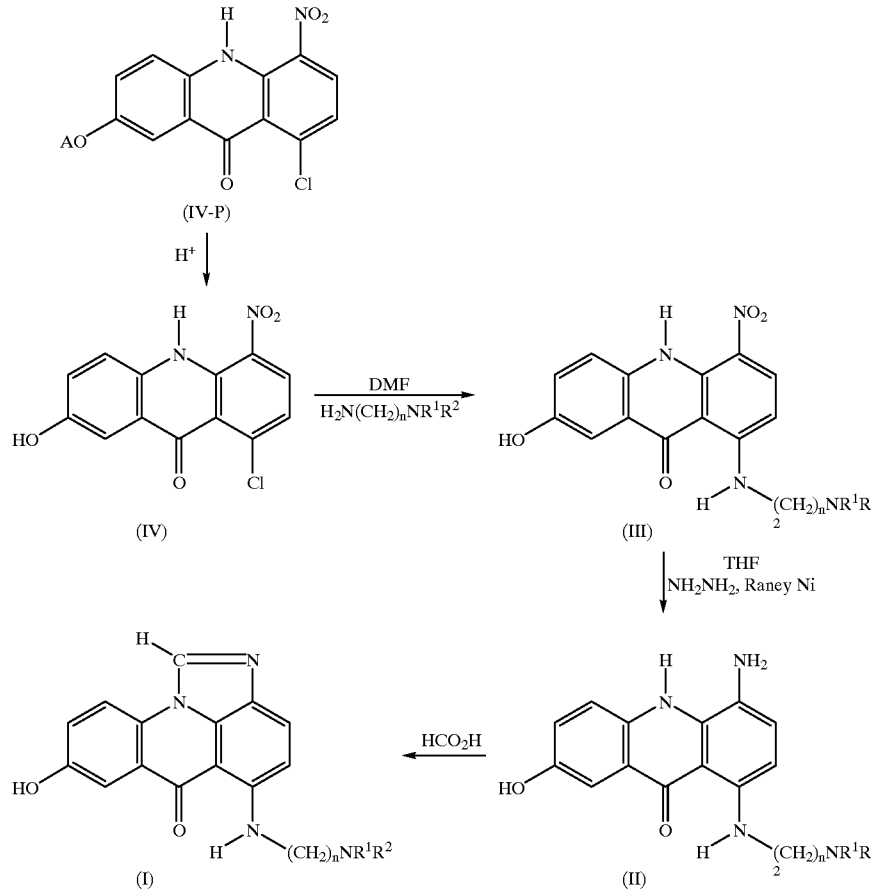

(A = a hydroxy-protecting group removable by reduction, $R^1$ and $R^2$ = $C_{1-4}$alkyl, n = 2 to 5)

It was a problem that the 7-hydroxy-4-amino-1-[[ω-(dialkylamino)alkyl]amino]acridin-9(10H)-one compounds of formula II are unstable. See particularly W. Cholody et al. J. Med. Chem. 35, 378–382 (1992), at page 379, right-hand column. This problem might be overcome by running the reduction and cyclisation as a single step in a "one pot reaction", by heating the nitro compounds of formula III with Raney nickel and formic acid. This reaction was carried out in the context of synthesising some imidazo[4,5,1-de][1,4]-diazepino[5,6,7-mn]acridines, see W. Cholody et al., J. Heterocyclic Chem. 29, 1749–1752 (1992). This procedure does not require isolation of the unstable amine (II).

benefit. Namely, the order of the operations of deprotecting the hydroxy groups and reacting the 4-chloro compound with the amine could be reversed and the deprotection could then be carried out in the same one-step reaction as the reduction and cyclisation. By this means three reactions can be carried out in one step, thus reducing the overall number of steps from four to two.

The reduction reaction produces an N-formyl compound as intermediate. This N-formyl compound is then cyclised. The overall Scheme is shown below as Scheme 2:

Scheme 2

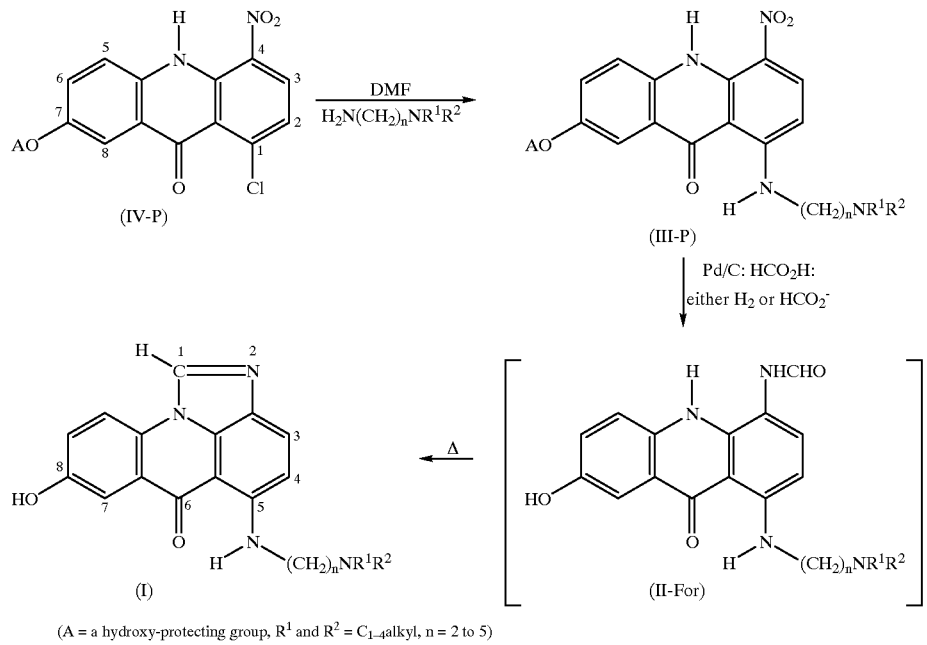

(A = a hydroxy-protecting group, $R^1$ and $R^2$ = $C_{1-4}$alkyl, n = 2 to 5)

Unfortunately, however, another problem arose. The purification of the preferred compound 5-[[2-(diethylamino)ethyl]amino]-8-hydroxyimidazo[4,5,1-de]acridin-6-one, of formula I, wherein $R^1$ and $R^2$ are ethyl and n is 2, free of nickel ions is difficult because both the compound and nickel ions are soluble in acidic solution, but precipitated by adding alkali. This is a serious problem, expected to arise to a greater or less degree with all the compounds of formula I, especially as they are intended for pharmaceutical use.

When, to avoid contamination by nickel ions, the reduction-cyclisation mixture composed of Raney nickel and formic acid was replaced by formic acid and palladium, the product compounds of formula (I) decomposed slowly during the reaction.

SUMMARY OF THE INVENTION

It has now been found that the last-mentioned problem can be solved if the reduction is carried out in formic acid at room temperature or slightly above, in the presence of palladium catalyst and either (a) a hydrogen-provider such as hydrogen gas or (b) formate ions, substantially all the palladium catalyst is removed and the substantially palladium-free solution is heated to effect cyclisation. Further, this method provided an unexpected, additional Accordingly, the present invention provides a process of preparing a compound of formula (I):

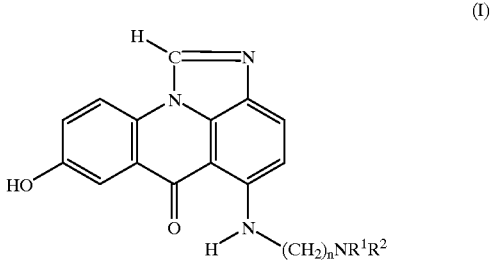

(I)

wherein $R^1$ and $R^2$ are alkyl groups of 1 to 4 carbon atoms and n is from 2 to 5, which comprises reacting a 1-chloro-7-(protected hydroxy)-4-nitroacridin-9(10H)-one of Formula (IV-P):

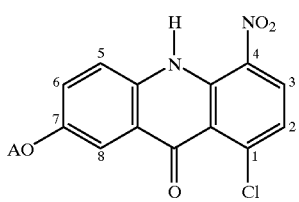

(IV-P)

wherein A is a hydroxy-protecting group removable by reduction, with an ω-(dialkylamino)alkylamine of formula

NH$_2$—(CH$_2$)$_n$NR$^1$R$^2$ in which n, R$^1$ and R$^2$ are as defined above, to produce a 7-(protected hydroxy)-4-nitro-1-[[ω-(dialkylamino)alkyl]amino]acridin-9(10H)-one of formula (III-P):

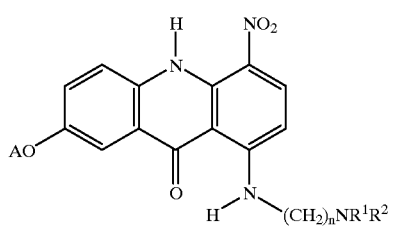

(III-P)

in which A, n, R$^1$ and R$^2$ are as defined above, reducing the compound of formula (III-P) at a temperature of from 15 to 50° C. with a reducing agent stronger than formic acid, such as hydrogen gas or formate anions, in the presence of a palladium catalyst and formic acid, removing substantially all the residual palladium and heating the remaining reaction mixture, typically at a temperature above 50° C., to effect cyclisation to the corresponding compound of formula (I).

The compound of formula (I), if produced as an addition salt, may be converted to the free base and vice versa. Any known procedures for these purposes may be used.

The invention further includes the N-formyl compounds (II-For) of formula shown in Scheme 2 per se, their preparation by isolation from the above-described filtrate from which substantially all the palladium has been removed, and their conversion to the corresponding compound of formula I comprising heating to effect cyclisation.

DESCRIPTION OF THE PREFERRED EMBODIMENTS

The process of the invention requires as starting material a 4-nitro-1-chloro compound of formula (IV-P) in which the hydroxy group is protected. These compounds IV-P can be prepared by preliminary steps shown in Scheme 3 below:

Scheme 3

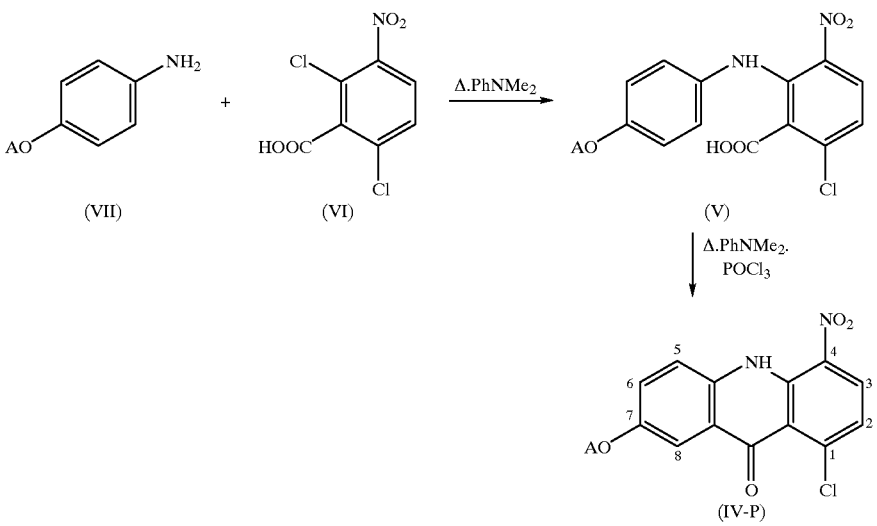

(A = a hydroxy-protecting group as defined above)

The hydroxy-protecting group, A, may be any which prevents the —OH from reacting with the carboxylic acid function of the benzoic acid derivative in Scheme 3 and may be removed by reduction, preferably benzyl (PhCH$_2$—). Other such usable protecting groups include allyl, 4-(dimethylaminocarbonyl)benzyl or arylbenzyl carbonate.

An example of a preparation in accordance with Scheme 3 can be found in Example 2 of European Patent EP-B-0145226 (Warner-Lambert Co.), the disclosure of which is herein incorporated by reference.

Turning now to the process of the invention shown in Scheme 2, the amination step may be carried out in any of the ways described in PCT Application WO-A-92/15583 or in European Patent EP-B-0145226, the disclosures of which in relation thereto are herein incorporated by reference. Preferably amination is by heating at moderately elevated temperature, e.g. 40 to 80° C., in an inert solvent such as dimethylformamide.

The preferred classes of compounds of formula (I) are those in which n is 2 or 3; also those in which $R^1$ and $R^2$ are the same, especially both methyl or both ethyl, so the same preferences (separately or together) apply to the amine reactant.

The reduction can be carried out by using hydrogen gas. While this reaction is best carried out at room temperature, say 15–30° C., the benefits of the invention are diminished, but not extinguished, at higher temperatures up to 50° C., especially up to 40° C. Alternatively the reduction can be carried out by using a salt of formic acid, for example ammonium formate, instead of hydrogen, and raising the temperature to between 30 and 50° C. In either case, formic acid, preferably at 80–98% w/v in water, is used. Preferably the formic acid is at 90–97% strength. The palladium catalyst may be present in any amount conventional in this reaction. It is removed from the reaction after reduction is judged to be complete, which is usually within the range 5 to 30 hours, typically 20 hours, at room temperature, depending on the amount of catalyst and stirring rate, and a correspondingly shorter time at slightly elevated temperature. Conveniently it is removed by filtration. The resultant reaction mixture, substantially free of palladium, is then heated to effect cyclisation, preferably to a temperature of above 50° C. and preferably from 80° C. up to reflux. No additional solvent is necessary, formic acid serving this purpose.

The cyclisation reaction is preferably carried out in the presence of a strong acid (a term which excludes formic acid, which is considered a weak acid), most preferably one which will form a pharmaceutically acceptable salt such as hydrochloric or methanesulphonic acid. Sulphuric acid is less preferred. Use of hydrochloric acid has been found to shorten the reaction time from 48 to 10 hours.

The compound of formula (I), obtained as the acid addition salt in the preferred method or by acidifying the free base, may be purified by crystallisation. The preferred compound (n=2, $R^1=R^2=C_2H_5$) may be crystallised from water or ethanol-water. Conveniently it is dissolved in hot 50% v/v aqueous ethanol, additional ethanol is optionally added and the solution allowed to crystallise.

The novel process avoids deprotection of 7-hydroxy group in a separate step, and thus avoids operation with the possibly mutagenic hydroxy intermediate. The new intermediate (III-P) can be prepared from chloro derivative (IV-P) with very good yields and is easy to purify. The process avoids operations involving free, very unstable amine (II), and does not involve isolation of the amine even as a salt. Further, it avoids the problem of contamination of the potential pharmaceutical product by metal ions derived from Raney nickel.

Alternatively, the reaction mixture, substantially free of palladium, is treated to work up the N-formyl compound (II-For), at a temperature below 40° C. This compound can then be crystallised and cyclised by heating in a solvent, to give the corresponding compound I. The compounds II-For show an anti-neoplastic, especially anti-leukaemia, effect and are thus useful in their own right as well as intermediates in the preparation of compounds I.

The present invention will now be described further by way of illustration only by reference to the following non-limiting Examples. Further embodiments of the invention will occur to those skilled in the art in the light of these.

EXAMPLES

Example 1

1. Preparation of 1-[[2-(diethylamino)ethyl]amino]-7-benzyloxy-4-nitroacridin-9(10H)-one (III-P)

A mixture of 7-benzyloxy-1-chloro-4-nitroacridin-9 (10H)-one (IV-P) (9.52 g, 25 mmol), 2-diethylaminoethylamine (4.3 ml, 30 mmol) and triethylamine (3.5 ml, 25 mmol) in dimethylformamide or dimethyl sulphoxide (150 ml) was stirred and heated at 60° C. for 1 hour. Next water (500 ml) and a concentrated solution of sodium carbonate (40 ml) were added and the precipitate was filtered, washed with water and dried to give 10.8 g (94%) of crude product. Crystallisation from dimethylformamide (100 ml) gave analytically pure product, yield 10 g (87%).

2. Preparation of 5-[[2-(diethylamino)ethyl]amino]-hydroxy-imidazo[4,5,1-de]acridin-6-one Dihydrochloride (I)

A mixture of 1-[[2-(diethylamino)ethyl]amino-7-benzyloxy-4-nitroacridin-9(10H)-one (III-P) (9.2 g, 20 mmol) and 10% palladium on charcoal (1 g) in 96% formic acid (100 ml) was hydrogenated, by bubbling in hydrogen gas, at room temperature for 24 hours. Next the catalyst was filtered off, and the filtrate was heated at 90° C. for 48 hr. (Alternatively, concentrated hydrochloric acid (5 ml) was added and the reaction time reduced to 10–15 hr). The solvent was evaporated under vacuum, the residue treated with 150 ml of hot 50/50 solution of concentrated hydrochloric acid and methanol, cooled and filtered to give the crude product (7 g, 79%). The crude product was refluxed in 50% ethanol (30 ml) with charcoal (1.5 g) for 5 min. The hot solution was filtered, 95% ethanol (100 ml) was added and the solution was left for crystallisation for 20 hours. The product was filtered and washed with ethanol to give yellow crystals of the product (6.4 g, 72%).

Example 2

1. Preparation of 5-[[2-(diethylamino)ethyl]amino]-8-hydroxy-imidazo[4,5,1-de]-acridin-6-one Dihydrochloride (I)

A mixture of 1-[[2-(diethylamino)ethyl]amino-7-benzyloxy-4-nitroacridin-9(10H)-one (III-P) (2.3 g, 5 mmol), ammonium formate (2.5 g) and 10% palladium on charcoal (0.25 g) in 96% formic acid (25 ml) was stirred at 40° C. until completion of the reaction as judged by TLC, typically 20 hours. Next the catalyst was filtered off, and the filtrate was heated at 90° C. for 48 hr. (Alternatively, concentrated hydrochloric acid (1 ml) was added and the reaction time reduced to 10–15 hours). The solvent was evaporated under vacuum, the residue treated with 150 ml of hot 50/50 solution of concentrated hydrochloric acid and methanol, cooled and filtered to give the crude product (71. g, 77%). The product can be purified as described above in Example 1.

2. Preparation of 1-[[2-(diethylamino)ethyl]amino]-7-hydroxy-4-(N-formylamino)acridin-9(10H)-one (II-For)

Part 1 of this Example was repeated up to filtering off the catalyst. Then the solvent was evaporated from the filtrate under vacuum at a temperature below 40° C. The residue was dissolved in methanol and product precipitated with diethyl ether. The purification procedure was repeated three times to give a yellow hygroscopic solid. The solid was dissolved in water and made alkaline with sodium bicarbonate, to give a yellow precipitate. The precipitate was crystallised from DMF-methanol to give the title compound, (540 mg. 27%).

The product was analysed by C,H,N elemental analysis, 500 MHZ $^1$H NMR, homoCOSY and $^{13}$C NMR. The data confirm the proposed structure and demonstrate that, at least in DMSO solution, the compound exists as a 1:2 mixture of two isomers of different orientations of the N-formyl group.

3. Anti-neoplastic Properties of II-For

The N-formyl compound (II-For) was screened for anti-neoplastic activity in mice injected i.p. with P388 lymphatic leukaemia cells and treated i.p. on days 1–5 (see WO-A-92/15583 for further details of the test). Results were as follows:

| dose (mg/kg) | % T/C* |
|---|---|
| 12.5 | 110 |
| 25 | 130 |
| 50 | 140 |
| 100 | 140 |
| 200 | 20 |

*ratio of medium survival time of the treated to the control mice expressed as a percentage.

What is claimed is:

1. A process of preparing a compound of formula (I):

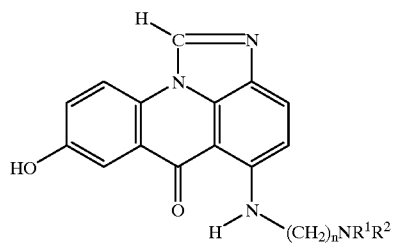

(I)

wherein $R^1$ and $R^2$ are alkyl groups of 1 to 4 carbon atoms and n is from 2 to 5, which comprises reacting a 1-chloro-7-(protected hydroxy)-4-nitroacridin-9(10H)-one of formula (IV-P):

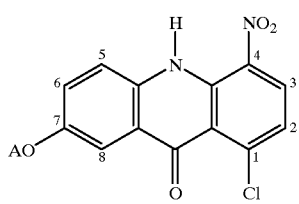

(IV-P)

wherein A is a hydroxy-protecting group removable by reduction, with an ω-(dialkylamino)alkylamine of formula

$NH_2-(CH_2)_nNR^1R^2$ in which n, $R^1$ and $R^2$ are as defined above, to produce a 7-(protected hydroxy)-4-nitro-1-[[ω-(dialkylamino)alkyl]amino]acridin-9(10H)-one of formula (III-P):

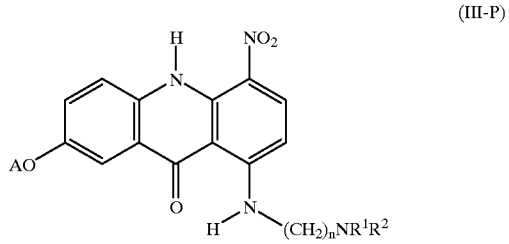

(III-P)

in which A, n, $R^1$ and $R^2$ are as defined above, reducing the compound of formula III-P at a temperature of from 15 to 50° C. with either a hydrogen-provider comprising a reducing agent able to reduce the nitro substituent and deprotect the hydroxy group in formic acid solution, or with formate ions, in the presence of a palladium catalyst and formic acid, removing substantially all the residual palladium and heating the remaining reaction mixture to effect cyclisation to the corresponding compound of formula I.

2. A process according to claim 1 wherein the reduction is carried out with hydrogen gas at 15 to 30° C.

3. A process according to claim 1 wherein the reduction is carried out with ammonium formate at a temperature of from 30 to 50° C.

4. A process according to claim 1, wherein the cyclisation is carried out in the presence of a strong acid.

5. A process according to claim 1 wherein the cyclisation is carried out in a solvent at a temperature of from 80° C. to the reflux temperature of the solvent.

6. A process according to claim 1 wherein the compound of formula IV-P is one in which the protected hydroxy group is a benzyloxy group.

7. A process according to claim 1 wherein the compound of formula I is obtained as an acid addition salt or is converted from the free base into an acid addition salt and the acid addition salt is crystallised from an ethanol-water mixture.

8. A process according to claim 1 wherein the amine is one in $R^1$ and $R^2$ are both methyl or both ethyl.

9. A process according to claim 8 wherein n is 2 and $R^1$ and $R^2$ are both ethyl.

10. A compound of the formula II-For:

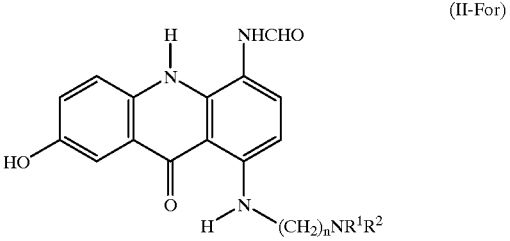

(II-For)

wherein $R^1$ and $R^2$ are alkyl groups of 1 to 4 carbon atoms and n is from 2 to 5.

11. A compound according to claim 10 wherein $R^1$ and $R^2$ are ethyl groups and n is 2.

* * * * *